(12) United States Patent
Weinberg et al.

(10) Patent No.: US 11,607,285 B2
(45) Date of Patent: Mar. 21, 2023

(54) APPARATUS, SYSTEM AND METHODOLOGIES FOR BIOPSY OR REMOVAL OF TISSUE OR ADDING MATERIAL TO TISSUE USING A MAGNETICALLY-ACTUATED CAPSULE

(71) Applicant: Weinberg Medical Physics, Inc., North Bethesda, MD (US)

(72) Inventors: Irving N. Weinberg, North Bethesda, MD (US); Amit Vohra, Rocklin, CA (US)

(73) Assignee: Weinberg Medical Physics, Inc

( * ) Notice: Subject to any disclaimer, the term of this patent is extended or adjusted under 35 U.S.C. 154(b) by 135 days.

(21) Appl. No.: 16/053,247

(22) Filed: Aug. 2, 2018

(65) Prior Publication Data

US 2019/0038370 A1 Feb. 7, 2019

Related U.S. Application Data

(60) Provisional application No. 62/540,358, filed on Aug. 2, 2017.

(51) Int. Cl.
| | |
|---|---|
| *A61B 34/00* | (2016.01) |
| *A61B 10/04* | (2006.01) |
| *A61B 10/02* | (2006.01) |
| *A61B 5/05* | (2021.01) |
| *A61B 5/06* | (2006.01) |
| *A61M 25/01* | (2006.01) |
| *A61B 34/20* | (2016.01) |

(52) U.S. Cl.
CPC ............... *A61B 34/73* (2016.02); *A61B 5/05* (2013.01); *A61B 5/062* (2013.01); *A61B 10/0283* (2013.01); *A61B 10/04* (2013.01); *A61M 25/0127* (2013.01); *A61B 2034/2051* (2016.02); *A61B 2034/2055* (2016.02); *A61B 2034/2059* (2016.02); *A61B 2034/2072* (2016.02); *A61B 2034/733* (2016.02); *A61B 2562/162* (2013.01)

(58) Field of Classification Search
CPC . A61B 10/02; A61B 10/0233; A61B 10/0266; A61B 10/0275; A61B 10/0283; A61B 10/04; A61B 17/320016; A61B 17/32002; A61B 17/320783; A61B 17/3403; A61B 17/3468; A61B 2010/0208; A61B 2017/320024; A61B 2017/320028; A61B 2017/320032; A61B 2034/2051; A61B 34/73; A61B 5/06; A61B 5/061; A61B 5/062; A61M 25/0127
See application file for complete search history.

(56) References Cited

U.S. PATENT DOCUMENTS

| | | | | |
|---|---|---|---|---|
| 5,830,224 | A * | 11/1998 | Cohn ..................... | A61B 17/11 606/167 |
| 8,154,286 | B2 | 4/2012 | Weinberg | |
| 8,172,865 | B2 * | 5/2012 | DeBoer ............... | A61F 9/00736 606/167 |
| 8,528,563 | B2 * | 9/2013 | Gruber .................. | A61B 1/303 128/832 |
| 8,545,529 | B2 * | 10/2013 | Underwood ..... | A61B 17/32002 606/171 |

(Continued)

*Primary Examiner* — Ryan J. Severson
(74) *Attorney, Agent, or Firm* — Barnes & Thornburg LLP

(57) ABSTRACT

Disclosed embodiments provide a biopsy tool and methodologies for obtain biopsies and/or a tool and methodology that may be used to add material to a subject's tissue.

23 Claims, 3 Drawing Sheets

(56) References Cited

U.S. PATENT DOCUMENTS

| | | | |
|---|---|---|---|
| 8,702,702 B1* | 4/2014 | Edwards | A61B 17/32002 606/48 |
| 9,216,031 B2* | 12/2015 | Mark | A61B 10/0275 |
| 9,301,770 B2* | 4/2016 | Gruber | A61B 1/303 |
| 9,380,959 B2 | 7/2016 | Weinberg et al. | |
| 10,290,404 B2* | 5/2019 | Mair | B82B 3/0066 |
| 2008/0245371 A1* | 10/2008 | Gruber | A61B 1/303 128/831 |
| 2009/0088784 A1* | 4/2009 | DeBoer | A61B 17/32002 606/167 |
| 2012/0157909 A1* | 6/2012 | Underwood | A61B 17/32002 604/22 |
| 2014/0107404 A1* | 4/2014 | Gruber | A61B 1/303 600/37 |
| 2016/0096030 A1 | 4/2016 | Nacev et al. | |
| 2016/0125994 A1 | 5/2016 | Mair et al. | |
| 2017/0172604 A1* | 6/2017 | Denham | A61B 17/32053 |
| 2017/0227617 A1 | 8/2017 | Weinberg et al. | |
| 2017/0258512 A1* | 9/2017 | Germain | A61B 17/1633 |
| 2019/0038370 A1* | 2/2019 | Weinberg | A61B 5/05 |
| 2019/0261846 A1* | 8/2019 | Oh | A61B 8/4209 |
| 2019/0269431 A1* | 9/2019 | Akilian | A61B 17/32002 |

* cited by examiner

APPARATUS, SYSTEM AND METHODOLOGIES FOR BIOPSY OR REMOVAL OF TISSUE OR ADDING MATERIAL TO TISSUE USING A MAGNETICALLY-ACTUATED CAPSULE

CROSS REFERENCE AND PRIORITY CLAIM

This patent application claims priority to U.S. Provisional Application Provisional Patent Application No. Patent Application Ser. No. 62/540,358, entitled "TOOL FOR BIOPSY OR ADDING TISSUES WITH MAGNETICALLY-ACTUATED APERTURE," filed Aug. 2, 2017, the disclosure of which being incorporated herein by reference in its entirety.

FIELD

Disclosed embodiments provide a tool for removing tissue from a subject's body

BACKGROUND

Conventional biopsy tools generally follow a straight path from the entry into a subject's body to the body tissue of interest. However, sometimes this path is not optimal because of important intervening structures.

In fact, even with beveled tipped biopsy tools, which allow for bending and maneuvering around such intervening structures, an insertion path may be very hard to predict or control. Additionally, conventional approaches may require multiple entry sites to obtain multiple biopsies.

SUMMARY

Disclosed embodiments provide a biopsy tool and methodologies for obtain biopsies and/or a tool and methodology that may be used to add material to a subject's tissue.

In accordance with at least one embodiment the tool may include a magnetically-actuated capsule.

In accordance with disclosed embodiments, such a tool may be implemented to provide additional flexibility for methodologies for performing a biopsy procedure by using an externally-applied magnetic field to manipulate and/or rotate a biopsy capsule within a tube.

In accordance with disclosed embodiments, such a tool may be used to introduce, or add, material to a subject's tissue. For example, the tool could be used in a procedure to introduce a particular type of medicine, supplement, micro- or nano-scale particles or other material to a subject's tissue.

DETAILED DESCRIPTION

As mentioned above, disclosed embodiments provide a biopsy tool and methodologies for obtain biopsies and/or a tool and methodology that may be used to add material to a subject's tissue. For the purposes of this specification, the term "subject" is understood to be a human or other animal with or without illness or injury, and the term "body" is understood to be one or more physical portions of the subject.

In accordance with at least one embodiment the tool may include a magnetically-actuated capsule. Thus, in accordance with disclosed embodiments, such a tool may be implemented to provide additional flexibility for methodologies for performing a biopsy procedure by using an externally-applied magnetic field to manipulate and/or rotate a biopsy capsule within a tube.

Figure 1:
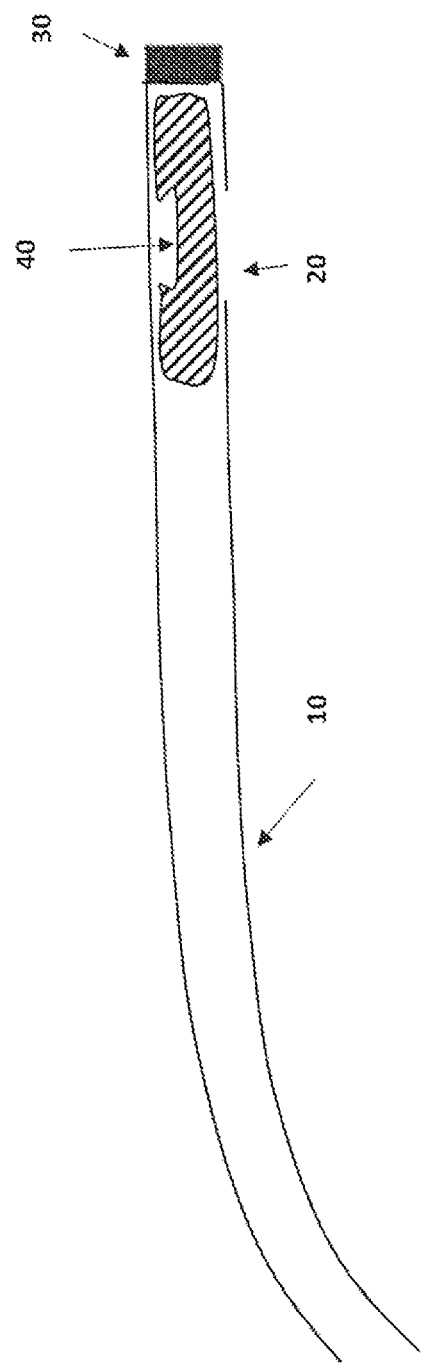
FIG. 1 illustrates an embodiment wherein a tube which may be flexible or rigid and may have a sharp tip or a beveled tip and which includes a hole or aperture through which tissues may be drawn into under suction.

FIG. 1 illustrates an embodiment of the invention. A tube 10, which may be flexible or rigid and may have a sharp and/or beveled tip, may include one or more holes or apertures 20 through which tissues may be drawn in under suction. Tube 10 may be composed of a flexible material (e.g., plastic) or of rigid materials or of combinations of rigid and flexible materials. The tube 10 may have a cap 30, which may be magnetizable.

Figure 2:
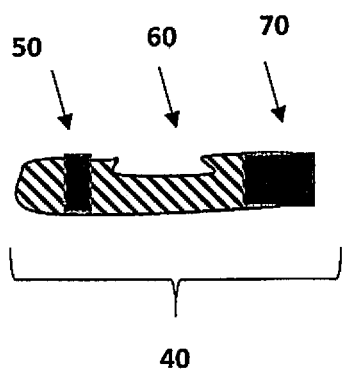
FIG. 2 illustrates an embodiment of a magnetically-actuated capsule according to the disclosed embodiments.

FIG. 2 illustrates an embodiment of capsule 40. In the embodiment, capsule 40 (which is at least partially hollow) contains a portion of magnetizable material (shown as a ring 50, which may be used to rotate the capsule 40 within tube 10. Capsule 40 contains at least one aperture 60 through which tissues may be drawn in under suction, or to add material (e.g. cells, scaffolding) to existing tissues in the body part. Capsule 40 may have additional sections including magnetizable materials 70 that may be used to manipulate capsule 40 and/or tube 10 within a body under the influence of a magnetic field.

Figure 3:
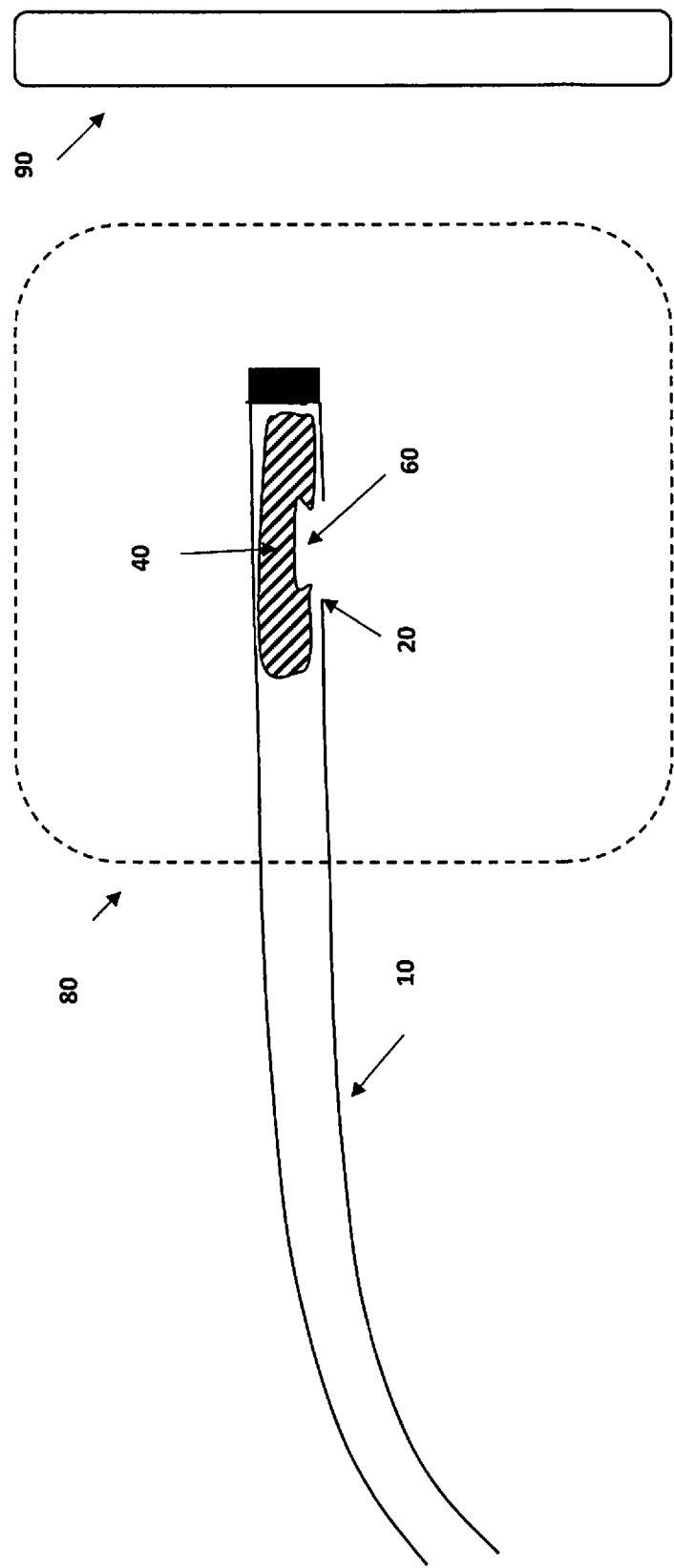
FIG. 3 illustrates an application or methodology disclosed herein wherein the tube is inserted into a subject's body part according to the disclosed embodiments.

FIG. 3 illustrates an embodiment of the invention. Capsule 40 in this illustration is shown with the capsule aperture 60 in the same direction as the tube hole 20, so that tissues can enter the capsule. A system for imaging and manipulating tube 10 and capsule 40 is shown schematically as part 90, at least some of which may be outside the body part 80.

Tube 10 may have a sharp and beveled tip so as to aid in insertion into the subject's body part. Air, another gas, fluid, wire, a spring or other material may be inserted into tube 10 to assist in inserting or removing capsule 40 within tube 10 and to remove or add fluid to the body part 90.

Thus, in accordance with at least one embodiment, tube 10 may be inserted into a subject's body part 80, the insertion being accomplished by way of a trocar, introducer, or other means of introduction.

In accordance with disclosed embodiments, such a tool may be used to introduce, or add, material to a subject's tissue. For example, the tool could be used in a procedure to introduce a particular type of medicine, supplement, micro- or nano-scale particles or other material to a subject's tissue. FIG. 3 illustrates an application of the invention, in which tube 10 is inserted into a body part 80. The tube may be inserted by way of a trocar or other introducer or as an attachment to a robot or tracker or under other guidance tools, which are not shown in FIG. 3.

It should be understood that control, coupling, and/or actuating mechanisms may be used to insert, withdraw, or manipulate air or fluid or other material to tube 10. Tube 10 may have one or more aperture 20 through which tissue, fluid or cells may be drawn under suction or expelled under pressure into tube 10 or into capsule 40 from the subject's body part.

The aperture 60 of capsule 40 may be configured to enable insertion or removal of tissues, for example, tissues drawn into capsule 40 under suction applied through the tube 10.

Thus, it should be understood that capsule 40 may contain one or more holes so that suction applied to tube 10 is transmitted through capsule 40 into capsule aperture 60 to draw tissues from the subject's body part into the capsule 40.

Suction mechanisms may be mechanical or battery or electrically operated. It should be understood that aperture 60 may have sharp edges, or have a shape that is conducive to cutting when capsule 40 is rotated or otherwise manipulated. It is understood that this removal of tissues may constitute a biopsy for the purposes of medical diagnosis or confirmation of diagnosis, or for removal of tissue for therapeutic purposes (e.g., for removal of cancerous or potentially cancerous tissue).

FIGS. 1 and 3 illustrate how capsule aperture 60 may be alternately aligned or dis-aligned with aperture 20 of tube 10 to facilitate a cutting action. It should be understood that the one or more apertures 20 may have one or more sharp edges (which may in some implementations also be retractable, or positioned only partially in the apertures 20 in the manner of a grater that includes one or more holes edged by slightly raised cutting edges) to facilitate cutting operation of capsule 40.

In accordance with at least one treatment or diagnostic methodology, tube 10 may be inserted into an o-ring so as to be placed inside the o-ring. Subsequently, the o-ring tube 10 combination may be inserted into a pump outlet tube (not shown).

Tube 10 may also have one or more magnetizable sections 30 which may be used to manipulate tube 10 into or in the subject's body part 80.

As shown in FIG. 2, capsule 40 may also contain a magnetizable section 50, which may be implemented as a ring or another structure configured to enable rotation of the capsule 40 within tube 10 by the application of one or more magnetic fields.

Capsule 40 may contain a magnetizable section 70 which may be used to manipulate capsule 40 within tube 10 or to manipulate tube 10 within the subject's body part 80.

Manipulation of capsule 40 within tube 10 can be accomplished with application of magnetic field by a system 90, wherein at least one of the components of system 90 being positioned externally to the subject's body part 80. The manipulation may include rotation of capsule 40 with respect to tube 10 to facilitate removal of tissues from body part 80, for example, by cutting connection between the subject's body tissue drawn into the capsule 40 and the subject's tissue still in the body part.

It should be understood that manipulation of capsule 40 and/or tube 10 may be effected using methods previously submitted for protection and published as US application 20160125994 by Lamar Mair et al, entitled "METHOD AND APPARATUS FOR NON-CONTACT AXIAL PARTICLE ROTATION AND DECOUPLED PARTICLE PROPULSION," incorporated herein by reference. That disclosure teaches, among other things, that it is possible to have multiple magnetizable sections of a particle that can be used to rotate and propel the particle.

In accordance with at least one embodiment, multiple transient magnetic fields (termed dynamic inversion) may be applied to capsule 40 or tube 10 to apply pulling or pushing actions, and for alternately imaging and propelling the capsule and tube within a body part, as taught by US patent application publication 20160096030, by Alek Nacev et al, entitled "PULSED GRADIENT FIELD METHOD TO COUNTERACT A STATIC MAGNETIC FIELD FOR MAGNETIC PARTICLE FOCUSING", and to U.S. Pat. No. 9,380,959 by Irving Weinberg et al, entitled "MRI-GUIDED NANOPARTICLE CANCER THERAPY APPARATUS AND METHODOLOGY" and to related submissions, both incorporated herein by reference.

It should be understood that the apparatus 90 for applying magnetic fields for imaging and/or manipulation may use electropermanent magnets, as taught by Irving Weinberg in US patent application publication 20170227617, entitled "METHOD AND APPARATUS FOR MANIPULATING ELECTROPERMANENT MAGNETS FOR MAGNETIC RESONANCE IMAGING AND IMAGE GUIDED THERAPY," incorporated herein by reference. The electropermanent magnets may at one or more times create a magnetic field configuration for imaging of a body part and/or tube and/or capsule, and then at another set of times create a magnetic field configuration for propulsion of the tube or capsule. It is understood that the imaging capability may be through magnetic resonance imaging methods.

It should be understood that the disclosed tool may be used in conjunction with other components, for example a computer and/or a power supply and/or coils for generating magnetic and/or electromagnetic fields, in order to attain a desired result of a meaningful image. It is understood that the image may use principles of proton magnetic resonance imaging, or magnetic resonance imaging of other particles (for example, electrons or sodium atoms) or other imaging principles (for example, magnetic particle imaging, or impedance imaging). It is understood that the apparatus may be used to deliver therapy by manipulating magnetizable materials with the magnetic field produced by the device. It should be understood that this manipulation may be performed at one time, and that imaging may be performed at another time, in order to guide the manipulation described above.

For the purpose of the disclosed embodiments, the term imaging, includes imaging technology that utilize components to form an image using magnetic resonance or magnetic particle imaging. It should be understood that such components include coils or magnets (or electro-permanent magnets) that polarize protons or other nuclei or electrons in one or more structures to be imaged, wherein gradient and/or radiofrequency coils form an image. Thus, although not shown in detail herein, it should be understood that the disclosed embodiments may be used in conjunction with a support structure that may hold an imaging system and may contain other components needed to operate or move the imaging system, for example, wheels and/or batteries. Moreover, it should be understood that an associated display system is not shown but should be understood to be present in order to view images produced by the imaging system.

It should be understood that one or more magnetic fields applied by system 90 to body part 80 may be so rapidly applied so as not to cause unpleasant nerve stimulation, as taught by Irving Weinberg in issued U.S. Pat. No. 8,154,286, entitled "APPARATUS AND METHOD FOR DECREASING BIO-EFFECTS OF MAGNETIC FIELDS" and related submissions by Irving Weinberg, incorporated herein by reference.

With the above description in mind, it is understood that the term "body part" means a tissue-containing structure in a living organism such as a human or other animal.

It should be understood that capsule 40 may be 10-cm or less in length, 1-cm or less in length, or 1-mm or less in length, or 100 microns or less in length, or 10 microns or less in length, or 1 micron or less in length. It is understood that capsule 40 may be 1-cm or less in width, or 1-mm or less in width, or 100 microns or less in width, or 10 microns or less in width, or 1 micron or less in width. It is understood that capsule 40 may be considered a particle for the purposes of correlation with prior inventions cited in this invention disclosure.

It should be understood that the term "magnetizable" and "magnetic" are used interchangeably to indicate a material that can be magnetized.

It should be understood that motion of a capsule within a tube implies both motion required to remove the capsule from the tube.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments of, as set forth above, are intended to be illustrative, not limiting. Various changes may be made without departing from the spirit and scope of the invention.

What is claimed:

1. An apparatus comprising:
   a capsule containing at least one aperture for removing or adding tissue from or to a subject's body part, the capsule having at least one magnetizable section containing a magnetizable material;
   a tube for manipulating the capsule therein and also including at least one aperture; and
   magnetic field generating means for generating and applying one or more magnetic fields to the subject's body part,
   wherein the manipulation of the capsule within the tube is performed using the magnetizable material influenced by the one or more magnetic fields, and
   wherein at least one portion of the magnetic field generating means is external to the subject's body part.

2. The apparatus of claim 1, wherein the aperture of the capsule is configured to be manipulated with respect to the tube via the one or more magnetic fields and wherein the capsule is removed from the tube to remove tissue from the subject's body part.

3. The apparatus of claim 1, wherein the aperture of the capsule is configured to be inserted into the tube and manipulated with respect to the tube via the one or more magnetic fields to add tissue to the subject's body part.

4. The apparatus of claim 1, wherein air or another gas, fluid, a wire or a spring or a combination of one or more of these elements, is introduced through the tube to facilitate removing tissue from the subject's body part.

5. The apparatus of claim 1, wherein air or another gas, fluid, a wire or a spring or a combination of one or more of these elements, is introduced through the tube to facilitate adding tissue, cells, or materials to or within the subject's body part.

6. The apparatus of claim 1, wherein air or another gas, fluid or a wire or spring or a combination of one or more of these elements, is introduced through the tube to facilitate additional movement of the capsule with respect to the tube or with respect to the subject's body part.

7. The apparatus of claim 1, wherein the tube includes means for attachment to a surgical or biopsy robot or a mechanical/magnetic/optical tracker.

8. The apparatus of claim 1, further comprising means for performing magnetic imaging of the subject's body part, wherein manipulation of the capsule or the tube into or in the subject's body part is performed under imaging guidance provided by the magnetic imaging.

9. The apparatus of claim 1, wherein the one or more magnetic fields have transition times that are too small to trigger unwanted side effects in the subject's body part.

10. The apparatus of claim 1, wherein the capsule has a length of 10 cm or less.

11. The apparatus of claim 1, wherein manipulation of the tube is performed using the magnetizable material of the capsule influenced by one or more further magnetic fields.

12. A method for removing tissue from a body part or adding material to a subject's body part, the method comprising:
   introducing a tube into the subject's body part, wherein the tube includes a capsule containing at least one aperture for removing or adding tissue from or to a subject's body part, the capsule having at least one magnetizable section containing a magnetizable material, wherein the tube also includes at least one aperture; and
   magnetically manipulating the capsule located within the tube within the subject's body part by generating and applying one or more magnetic fields to the magnetizable material in the subject's body part, wherein the one or more magnetic fields are generated outside and applied to the subject's body part by a system that is at least in part external to the subject's body.

13. The method of claim 12, further comprising manipulating the aperture of the capsule with respect to the tube via the one or more magnetic fields and removing the capsule from the tube to remove tissue from the subject's body part.

14. The method of claim 13, further comprising manipulating the tube by further magnetically manipulating the capsule located in the tube within the subject's body part by generating and applying one or more further magnetic fields to the magnetizable material.

15. The method of claim 12, further comprising inserting the capsule into the tube and manipulating the aperture of the capsule with respect to the tube via the one or more magnetic fields to add tissue to the subject's body part.

16. The method of claim 12, further comprising introducing air or another gas, fluid, a wire or a spring through the tube to facilitate removing tissue from the subject's body part.

17. The method of claim 12, further comprising introducing air or another gas, fluid, a wire or a spring through the tube to facilitate adding tissue, cells, or materials to or within the subject's body part.

18. The method of claim 12, further comprising introducing air or another gas, fluid, a wire or a spring through the tube to facilitate additional movement of the capsule with respect to the tube or with respect to the subject's body part.

19. The method of claim 12, further comprising attaching the tube to a surgical or biopsy robot or a mechanical/magnetic/optical tracker.

20. The method of claim 12, wherein manipulation of the capsule or the tube into or in the subject's body part is performed with propulsion applied using dynamic inversion.

21. The method of claim 12, further comprising magnetic imaging the subject's body part, wherein manipulation of the capsule or the tube into or in the subject's body part is performed under imaging guidance provided by the magnetic imaging.

22. The method of claim 12, wherein the one or more magnetic fields have transition times that are too small to trigger unwanted side effects in the subject's body part.

23. The method of claim 12, wherein the capsule has a length of 10 cm or less.

\* \* \* \* \*